United States Patent [19]

Grimberg

[11] Patent Number: 4,591,503

[45] Date of Patent: May 27, 1986

[54] COMPOSITION FOR IMPROVED ABSORPTION OF 2A CATIONS AND GOLD COMPRISING YEAST OR LACTOBACILLUS

[76] Inventor: Georges S. Grimberg, 123 rue de l'Université, 75007 Paris, France

[21] Appl. No.: 555,335

[22] Filed: Nov. 28, 1983

[30] Foreign Application Priority Data

Dec. 1, 1983 [FR] France .................................. 82 20124

[51] Int. Cl.⁴ ...................... A61K 33/30; A61K 33/26; A61K 37/00; A61K 33/00; A61K 33/38; A61K 33/36
[52] U.S. Cl. ........................................ 424/93; 424/127; 424/131; 424/132; 424/136; 424/139; 424/140; 424/145; 424/147
[58] Field of Search ............... 424/127, 131, 132, 136, 424/139, 140, 145, 147; 435/41, 174, 243, 244, 253, 255, 256, 267, 853, 854, 940, 942; 426/2, 62

[56] References Cited

U.S. PATENT DOCUMENTS 4,001,389 1/1977 Fildes et al. ........................... 424/17
4,035,479 7/1977 George et al. ........................ 424/78

FOREIGN PATENT DOCUMENTS 0503705 6/1954 Canada ................................ 424/50

OTHER PUBLICATIONS

Borbolla et al., Chem. Abst., vol. 93, No. 110330k, "Some Characteristics of Calcium Uptake by Yeast Cells".
Chemical Abstracts, vol. 88, 1978, No. 134839f, Fedorova, I. Yu et al. "Mineral Composition of Baker's Yeast".

Primary Examiner—Thomas G. Wiseman
Assistant Examiner—Robin Lyn Teskin
Attorney, Agent, or Firm—Browdy and Neimark

[57] ABSTRACT

A method for improving the absorption of pharmaceutical cations, in particular those of the 2A group and gold by orally administering the cations in combination with either yeast or Lactobacillus.

8 Claims, No Drawings

COMPOSITION FOR IMPROVED ABSORPTION OF 2A CATIONS AND GOLD COMPRISING YEAST OR LACTOBACILLUS

The present invention has for its object a combination enabling to improve absorption of pharmaceutical metallic cations by the human system, when these cations are administered orally whatever the valence of the cations.

According to the invention, the combination improving absorption of cations by the human system, and the medicaments thereof contain a pharmaceutically acceptable organic and/or inorganic salt admixed with a pharmaceutically acceptable microorganism.

There is already used for many years in human therapeutics orally admistered medications containing various calcium salts in some form.

After having administered increasing quantities of $Ca^{++}$, the common maximum dose is at present fixed to be 500 mg $Ca^{++}$, two to three times a day, and this is because larger dosages are not effectively absorbed.

The present invention has for its purpose to increase the amount of calcium that may be absorbed by a mammal, particularly a human being.

EXAMPLE 1

500 mg $Ca^{++}$ present as calcium salt
pharmaceutically acceptable yeast: 100 mg
pharmaceutical galenic and/or aromatic excipient in a sufficient quantity for one dose.

It has been found that the medicament which is the subject matter of the present invention can be formed by soluble or insoluble organic and/or inorganic calcium salt, and that, instead of the yeast, it is possible to use other microorganisms such as, for example, lactobacillus.

TOXICOLOGY

The LD 50 is of about 1,000 mg calcium per kilogram of the patient.

ANIMAL PHARMACOLOGY 100 weaning rats were submitted to a synthetic alimentary diet which was totally deficient in calcium.

20 weaning rats were submitted to a normal alimentary diet and have been considered as a reference batch.

The 100 deficient rats were divided into 5 batches of 20 rats each: 10 males, 10 females.

Deficient batch No. 1 received no $Ca^{++}$.

Deficient batch No. 2 received a preparation containing an organic salt of calcium and a corresponding quantity of a pharmaceutically acceptable yeast, such as brewer's yeast, the preparation being hereinafter called "Medicament A".

Deficient batch No. 3 received a preparation of the same organic salt of calcium as deficient batch No. 2 and in the same quantity but without any yeast, this preparation being hereinafter called "Medicament B".

Deficient batch No. 4 received a preparation containing an inorganic salt of calcium and a corresponding amount of a pharmaceutically acceptable yeast yeast, this preparation being hereinafter called "Medicament C".

Deficient batch No. 5 received the same preparation as deficient batch No. 4 and in the same quantity but without any yeast, this preparation being hereinafter called "Medicament D".

After a treatment of sixty days, the average calcium concentration in the rats was measured by known methods. The average calcium concentration in batches 2 and 4 was statistically higher than that of batches 3 and 5.

Moreover, the average calcium concentration in batches 2 and 4 were similar.

Therefore, the calcium-yeast medicament enables a beneficial improvement of calcic therapeutics.

CLINICAL PHARMACALOGY

Tests were conducted in accordance with the method taught by Bhandarkhar et al, in Brit. Med.J., 1961, 2, 15–39, as codified by Caniggia et al. 30 patients were divided into two groups of 15 patients.

10 microcuries of $Ca^{45}$ were added to Medicaments A, B, C, D.

Group I
received at the time $D_o$ the Medicament A+10 microcuries of $Ca^{45}$
received at the time $D_o+30$ (30 days after) the Medicament B+10 microcuries of $Ca^{45}$ Group II
Received at the time $D_o$ the Medicament D+10 microcuries of $Ca^{45}$
Received at the time $D_o+30$ the Medicament C+10 microcuries of $Ca^{45}$ Each patient is his own reference. A standard measure of radioactivity showed in a statistically significant manner that the Medicament A and the Medicament C are better absorbed than Medicament B and the Medicament D.

THERAPEUTICS

Various calcium deficient people received calcic therapeutics according to the invention and recovered their tonicity more rapidly than with conventional calcium substances used in calcium therapy.

EXAMPLE 2

The same kind of studies were made with magnesium. The animal pharmacology that magnesium sulfate with yeast gives a magnesium substance which is significantly better absorbed than magnesium sulfate alone.

The human pharmacology made with $Mg^{28}$ has similarly shown the role of the microorganism.

EXAMPLE 3

A radioactively marked gold salt was orally administered. With the microorganisms, there was obtained a better absorption of gold.

Copper, Tin, Cobalt, Zinc and Silver have also been checked, as well as other cations of any valence.

The above examples clearly demonstrate the role of microorganisms such as yeast in combination with a cation.

It should also be noted that the microorganism added to the preparation can be alive or dead, and that the medicament can be used in many therapeutically conventional forms.

Moreover the quantity of microorganism used in the medicamentous preparation can vary and be greater or smaller than the quantity of cations.

What is claimed is:

1. A method for improving the absorption of pharmaceutical metallic cations in a mammal, comprising the steps of admixing a pharmaceutically acceptable salt of a metallic cation selected from the group consisting of divalent and gold cations with an amount of pharmaceutically acceptable yeast or bacillus of the lactobacillus type effective to significantly increase the percentage of said metallic cation absorbed by said mammal over the percentage of said metallic cation which would be absorbed by said mammal if said metallic cation were administered without said yeast or lactobacillus to form a pharmaceutically acceptable medication, and orally administering a therapeutically effective amount of said medication to said mammal.

2. The method of claim 2 wherein said mammal is a human being.

3. The method of claim 2 wherein said pharmaceutically acceptable salt is inorganic.

4. The method of claim 7 wherein said pharmaceutically acceptable microorganism is a yeast.

5. The method of claim 5 wherein said pharmaceutically acceptable microorganism is alive.

6. The method of claim 1, wherein said metallic cation comprises calcium, magnesium or gold.

7. The method of claim 3, wherein said metallic cation comprises calcium.

8. The method of claim 4, wherein the weight ratio of said pharmaceutically acceptable yeast to said calcium ion is about 1:5.

* * * * *

UNITED STATES PATENT AND TRADEMARK OFFICE
CERTIFICATE OF CORRECTION

PATENT NO. : 4,591,503
DATED : May 27, 1986
INVENTOR(S) : Georges S. Grimberg

It is certified that error appears in the above-identified patent and that said Letters Patent is hereby corrected as shown below:

Claim 2 should read: The method of claim 6 wherein said mammal is a human being.

Claim 5 should read: The method of claim 3 wherein said pharmaceutically acceptable microorganism is alive.

Signed and Sealed this

Twenty-sixth Day of August 1986

[SEAL]

Attest:

Attesting Officer

DONALD J. QUIGG

Commissioner of Patents and Trademarks